US 6,817,364 B2

United States Patent
Garibaldi et al.

(10) Patent No.: US 6,817,364 B2
(45) Date of Patent: Nov. 16, 2004

(54) MAGNETICALLY NAVIGATED PACING LEADS, AND METHODS FOR DELIVERING MEDICAL DEVICES

(75) Inventors: Jeffrey M. Garibaldi, St. Louis, MO (US); Jonathan C. Sell, Eagan, MN (US); Roger N. Hastings, Maple Grove, MN (US); Andrew F. Hall, St. Charles, MO (US)

(73) Assignee: Stereotaxis, Inc., St. Louis, MO (US)

( * ) Notice: Subject to any disclaimer, the term of this patent is extended or adjusted under 35 U.S.C. 154(b) by 53 days.

(21) Appl. No.: 09/911,351

(22) Filed: Jul. 23, 2001

(65) Prior Publication Data

US 2002/0116043 A1 Aug. 22, 2002

Related U.S. Application Data

(60) Provisional application No. 60/220,525, filed on Jul. 24, 2000.

(51) Int. Cl.[7] .................................................. A61N 1/05

(52) U.S. Cl. ........................................ 128/899; 600/585

(58) Field of Search .............................. 604/264, 510, 604/523, 528; 128/899; 607/122; 600/101, 585

(56) References Cited

U.S. PATENT DOCUMENTS

| | | | | |
|---|---|---|---|---|
| 3,674,014 A | * | 7/1972 | Tillander | 600/434 |
| 3,941,119 A | * | 3/1976 | Corrales | 600/434 |
| 4,244,362 A | * | 1/1981 | Anderson | 128/200.26 |
| 5,304,218 A | | 4/1994 | Alferness | |
| 5,492,538 A | * | 2/1996 | Johlin, Jr. | 604/264 |
| 5,639,276 A | * | 6/1997 | Weinstock et al. | 606/129 |
| 5,755,766 A | | 5/1998 | Chastain et al. | |
| 5,800,497 A | * | 9/1998 | Bakels et al. | 607/122 |
| 5,803,928 A | | 9/1998 | Tockman et al. | |
| 5,843,153 A | * | 12/1998 | Johnston et al. | 607/122 |
| 5,902,331 A | | 5/1999 | Bonner et al. | |
| 5,931,818 A | * | 8/1999 | Werp et al. | 604/270 |
| 6,292,678 B1 | | 9/2001 | Hall et al. | |
| 6,385,472 B1 | * | 5/2002 | Hall et al. | 600/374 |
| 6,522,909 B1 | * | 2/2003 | Garibaldi et al. | 600/424 |

* cited by examiner

*Primary Examiner*—Kennedy Schaetzle
(74) *Attorney, Agent, or Firm*—Harness, Dickey & Pierce, P.L.C.

(57) ABSTRACT

A method of placing a pacing lead in the heart includes introducing a distal end of a delivery catheter into the patient's vasculature; magnetically navigating the distal end of the delivery catheter to the patient's heart; deploying a pacing lead from the distal end of the delivery catheter; and magnetically navigating the pacing lead to the pacing application site.

9 Claims, 7 Drawing Sheets

MAGNETICALLY NAVIGATED PACING LEADS, AND METHODS FOR DELIVERING MEDICAL DEVICES

CROSS REFERENCE TO RELATED APPLICATION

This application claims priority of prior provisional application Ser. No. 60/220,525, filed Jul. 24, 2000.

FIELD OF THE INVENTION

This invention relates to magnetic navigation of medical devices, and in particular to improved methods and means for the delivery of bi-ventricular pacing leads.

BACKGROUND OF THE INVENTION

Bi-ventricular pacing is an increasingly used treatment of electrical irregularities of the heart, and particularly diseased and enlarged hearts. See, for example, U.S. Pat. Nos. 5,304, 218, 5,755,766, 5,800,497, 5,803,928, 5,902,331, and Mertz, Non-Traditional Pacemakers Synchronize Ailing Hearts, the contents of all of which are incorporated herein by reference. However the procedure of placing the pacing leads is difficult and time consuming. The length of the procedure puts patients, who usually already have diseased or damaged hearts, at risk, and makes the procedure relatively expensive.

SUMMARY OF THE INVENTION

The present invention provides a method and apparatus for guiding medical devices into human blood vessels. It is particularly useful for the placement of pacing leads and delivery catheters for facilitating the placement of the leads, and improved methods of placing the leads that make the procedures easier for the physicians to perform, and shorter for the patients. This reduces the stress of the procedure on the patient, and shortens recovery time.

BRIEF DESCRIPTION OF THE DRAWINGS

Corresponding reference numerals indicate corresponding parts throughout the drawings.

DETAILED DESCRIPTION OF THE INVENTION

The present invention provides a method and apparatus for placing pacing leads in the heart, and is particularly useful for the placement of pacing leads for bi-ventricular pacing. In accordance with the present invention, a delivery catheter 20, having a proximal end, a distal end 24 and a lumen 26 therebetween, is magnetically navigated until the distal end is at a selected deployment site in the heart, such as the coronary sinus, or more preferably the venous vasculature beyond the coronary sinus in which the pacing leads will be implanted. Pacing leads are then magnetically navigated from the distal end 24 of the delivery catheter 20 to the site of implantation.

There are several alternative ways to place a delivery catheter in the coronary vaslculature. The preferred way is through the superior vena cava to access the ostium of the coronary sinus. This twisted, tortuous path, requiring the placement of the distal end of the delivery catheter in a small opening in a large moving chamber, presents a difficult challenges for conventional navigation, but can be greatly facilitated with magnet assisted navigation, as described below.

Figure 1:
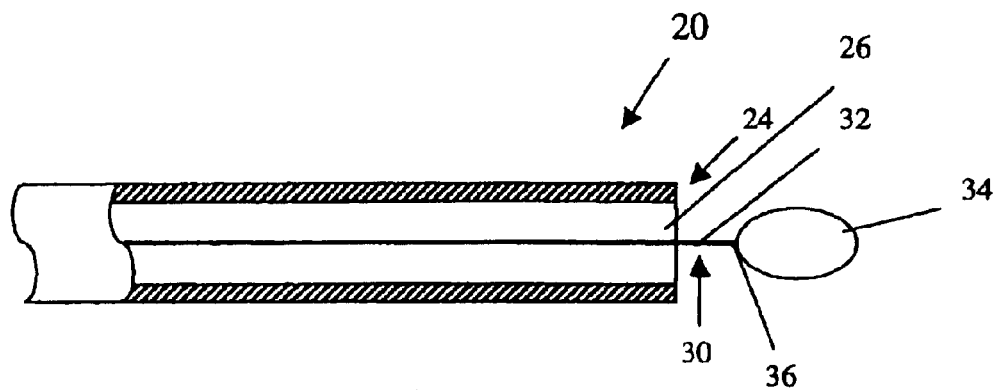
FIG. 1 is a partial cross-sectional view of the distal end of a delivery catheter used to deploy pacing leads in accordance with this invention, shown as it would be navigated with a guide wire.

According to a first embodiment of this invention shown in FIG. 1, the distal end 24 of the delivery catheter 20 is magnetically navigated to the deployment point in the heart by using a magnetic guide wire 30. The guide wire 30 comprises a flexible wire 32, having a proximal end and a distal end 36, with a magnetic body 34 on its distal end. The flexibility of the wire 32 may vary along its length, preferably increasing in flexibility toward the distal end 36. The magnetic body 34 may be either a permanent magnetic material or a permeable magnetic material, so long as the magnetic body is responsive to an externally applied magnetic field. The delivery catheter 20 and guide wire 30 are introduced into the patient's vasculature, and advanced through the vasculature by applying an external magnetic field in the appropriate direction to orient the magnetic body 34, and thus the distal end 36 of the guide wire 30, in the desired direction of movement. The guide wire 30 can then be advanced in the desired direction by pushing the proximal end. If the applied field includes a magnetic gradient, the field can also be used to advance the magnetic body, and thus the distal end of the guide wire, in the desired direction. The delivery catheter 20 is then advanced over the guide wire 30. The guide wire 30 is successively advanced ahead of the delivery catheter 20, and the delivery catheter is successively advanced over the guide wire, until the distal end of the delivery catheter reaches the deployment point.

Conventional, mechanically steered guiding catheters must be rigid enough to transmit torque to the distal end for steering. Thus, the target for these catheters is typically the ostium or opening of the blood vessel. These guide catheters cannot be safely advanced a significant distance into the vessel beyond the ostium because they are too rigid and/or the distal end has a fixed curved or angled shape. When medical devices, such as pacing leads or stent delivery systems, are advanced through these guide catheters into the distal vessel, the guide catheter often backs out of the ostium, which prevents the device from advancing further into the vessel. The problem can be severe enough to prevent advancement of the medical device to the target site. By contrast, the magnetically steered guide catheters of the present invention need not transmit torque, and they may have a soft and flexible distal section. They can be safely advanced a significant distance into the vessel beyond the ostium via magnetic coupling to the magnet on the distal tip of a flexible stylette. When the stylette is removed, medical devices can be advanced within the guide catheter to a point much closer to the target site in the vessel.

Figure 2:
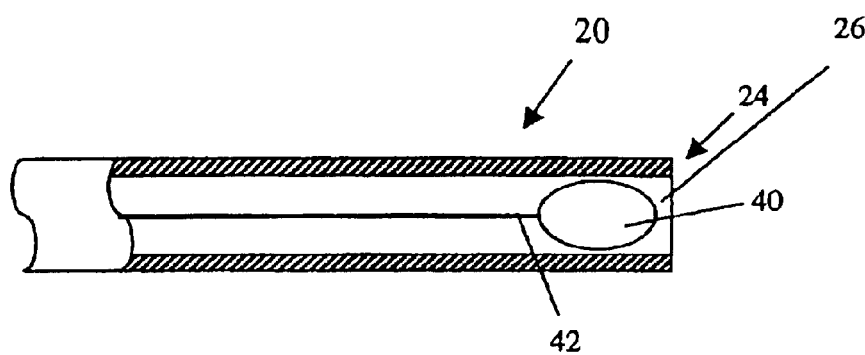
FIG. 2 is a partial cross-sectional view of the distal end of a delivery catheter used to deploy pacing leads in accordance with this invention, shown as it would be navigated with a tethered magnetic body.

According to a second embodiment of this invention shown in FIG. 2, the distal end 24 of the delivery catheter 20 is magnetically navigated to the deployment point in the heart by using a magnetic body 40, disposed in the lumen 26 of the delivery catheter, adjacent the distal end. The magnetic body 40 may be either a permanent magnetic material or a permeable magnetic material. The magnetic body 40 is attached to a tether 42 extending through the lumen 26 of the delivery catheter to the proximal end. The tether 42 helps retain the magnetic body 40 in the lumen 26 of the delivery catheter 20, and allows the magnetic body 40 to be withdrawn from the delivery catheter once the distal end 24 of the delivery catheter has been navigated to the deployment point. The delivery catheter 20 and magnetic seed 40 are introduced into the patient's vasculature, and advanced through the vasculature by applying an external magnetic field in the appropriate direction to orient the magnetic body 40, and thus the distal end 24 of the delivery catheter 20, in the desired direction of movement. The delivery catheter 20 can then be advanced by pushing the proximal end. If the applied field includes a magnetic gradient, the field can also be used to advance the magnetic body, and thus the distal end of the guide wire, in the desired direction. Once the distal end 24 of the delivery catheter 20 reaches the distribution point, the magnet body is removed through the lumen 26 by pulling the tether 42.

Figure 2A:
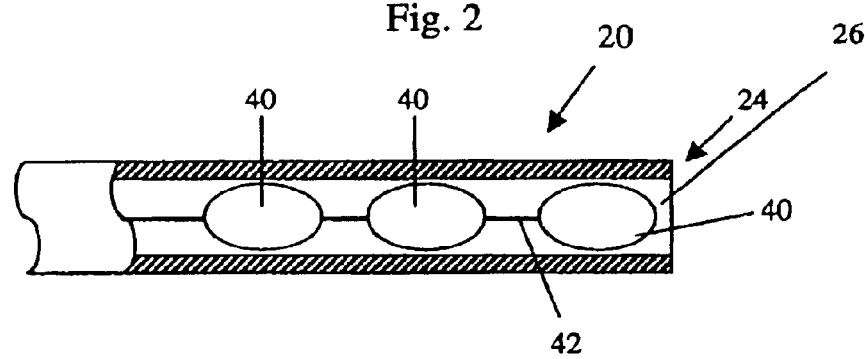
FIG. 2A is a partial cross-sectional view of the distal end of a delivery catheter used to deploy pacing leads in accordance with this invention, shown as it would be navigated with a plurality of tethered magnetic bodies.
Figure 13A:
FIG. 13A is a cross-sectional view of a cannula with a plurality of magnet bodies having different directions of magnetization disposed therein.
Figure 13B:
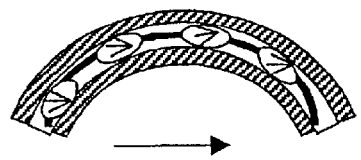
FIG. 13B is a cross-sectional view of the cannula shown in FIG. 13A after the application of a magnetic field, showing the tendency of the magnet bodies to shape the cannula.

An alternate construction of the second embodiment is shown in FIG. 2A, where instead of one magnetic body 40 on the distal end of the tether 42, there are a plurality of magnetic bodies 40 on the distal end portion of the tether. The plurality of magnetic bodies 40 facilitates the navigation of the distal end of the delivery catheter, causing the entire distal end portion to align with the field. While the magnetization direction of the magnetic bodies would conventionally be axial, parallel to the tether, in some applications it might be desirable to have the magnetization direction of each magnetic body 40 vary from axial so that when a magnetic field is applied to the magnet bodies 40 on the tether 42, the catheter 20 assumes a predetermined shape as the magnet bodies align with the applied magnetic field. This is illustrated in FIGS. 13A and 13B. In FIG. 13A, a plurality of magnetic bodies on a tether are disposed in the lumen of a flexible cannula. The magnetization direction of each of the magnetic bodies, indicated by arrows, is selected so that when a magnetic field is applied the magnetic bodies cause the portion of the flexible cannula in which they are positioned, to assume a predetermined shape. This is shown in FIG. 13B, where the magnet bodies cause the cannula to assume a curved shape. The material of the cannula inherently resists flexing, so the shape of the cannula is somewhat dependent upon the strength of the applied field. The stronger the field, the more closely the cannula conforms to the designed shape, and the weaker the field the more the cannula varies from the applied field. This gives the user some control over the shape of the cannula.

Figure 3:
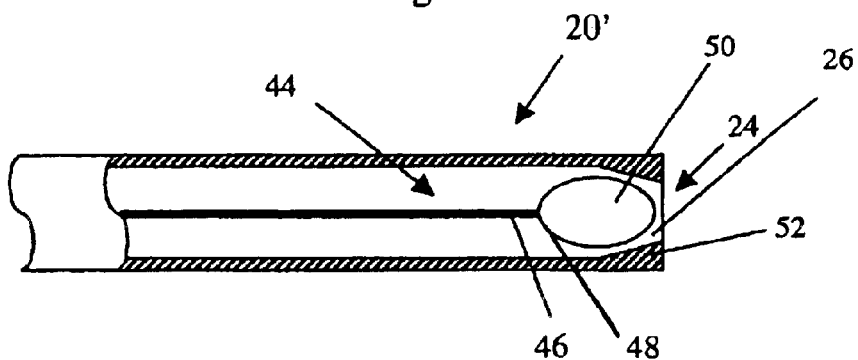
FIG. 3 is a partial cross-sectional view of the distal end of a delivery catheter used to deploy pacing leads in accordance with this invention, shown as it would be navigated with a magnetic stylette.

According to a third embodiment of this invention shown in FIG. 3, the distal end 24 of the delivery catheter 20' is magnetically navigated to the deployment point in the heart by using a magnetic stylette 44, disposed in the lumen 26 of the delivery catheter 20'. The catheter 20' is similar to catheter 20, except that catheter 20' includes an annular collar in the lumen, as described below. The stylette 44 comprises a flexible shaft 46 having a proximal end, a distal end 48, and a magnetic body 50 on the distal end. The shaft 46 is sufficiently flexible to allow the stylette to flex under the applied magnetic field and conform to the tortuous path through the vasculature, but is sufficiently stiff to apply a pushing force to the delivery catheter 20'. The stylette 44 can be inserted into the lumen 26 of the delivery catheter 20', with the distal end of the stylette engaged by a stricture formed by an annular collar 52 on the inside of the lumen 26, so that the magnetic body 52 of the stylette is retained in the lumen. Once the delivery catheter 20' is at the deployment site, the stylette 44 can be removed from the lumen 26. The delivery catheter 20' with the stylette 44 in the lumen 26 are introduced into the patient's vasculature, and advanced through the vasculature by applying an external magnetic field in the appropriate direction to orient the magnetic body 50, and thus the distal end 24 of the delivery catheter 20, in the desired direction of movement. If the applied field includes a magnetic gradient, the field can also be used to advance the magnetic body, in the desired direction. The delivery catheter 20' can then be advanced by pushing the proximal end of either the delivery catheter 20', or preferably of the stylette 44. Once the distal end 24 of the delivery catheter 20' reaches the deployment point, the stylette 44 is withdrawn from the delivery catheter through the proximal end.

Figure 3A:
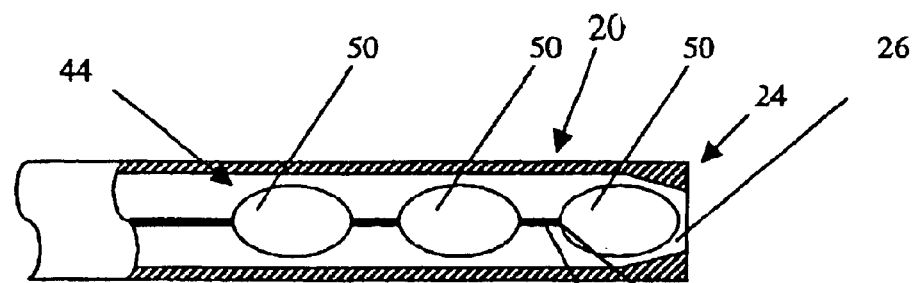
FIG. 3A is a partial cross-sectional view of the distal end of a delivery catheter used to deploy pacing leads in accordance with this invention, shown as it would be navigated with a magnetic stylette with multiple magnetic bodies.

An alternate construction of the third embodiment is shown in FIG. 3A, where instead of one magnetic body 50 on the distal end of the stylette 44, there are a plurality of magnetic bodies 50 on the distal end portion of the stylette. The plurality of magnetic bodies 50 facilitates the navigation of the distal end of the delivery catheter, causing the entire distal end portion to align with the field. While the magnetization direction of the magnetic bodies would conventionally be axial, parallel to the shaft of the stylette 44, in some applications it might be desirable to have the magnetization direction of each magnetic body 50 vary from axial so that when a magnetic field is applied to the magnet bodies 40 on the stylette 42, the catheter 20' assumes a predetermined shape as the magnet bodies align with the applied magnetic field. This is illustrated in FIGS. 13A and 13B, and described above.

Figure 4:
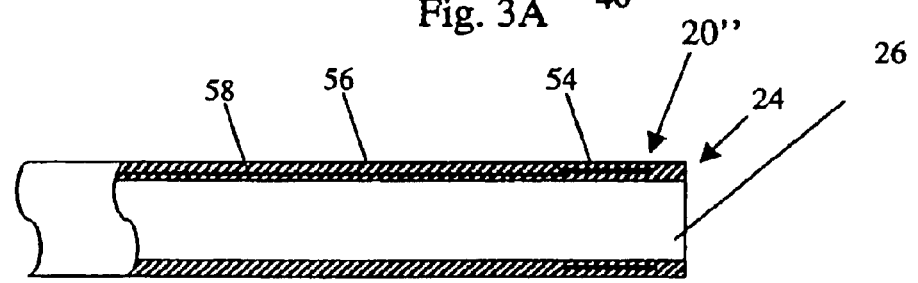
FIG. 4A is a partial cross-sectional view of the distal end of a delivery catheter used to deploy pacing leads in accordance with this invention, with an inflatable chamber for facilitating magnetic navigation of the delivery catheter, shown with the inflatable chamber uninflated.
FIG. 4B is a partial cross-sectional view of the distal end of a delivery catheter used to deploy pacing leads in accordance with this invention, with an inflatable chamber for facilitating magnetic navigation of the delivery catheter, shown with the inflatable chamber inflated.
Figure 4A:
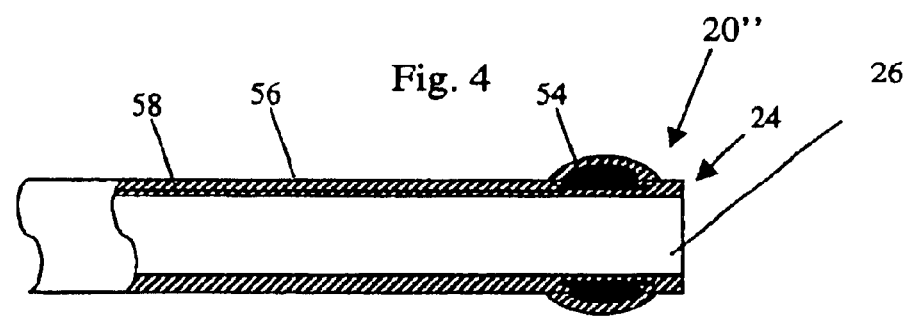

According to a fourth embodiment of this invention shown in FIGS. 4 and 4A, the distal end 24 of a specially constructed delivery catheter 20" is magnetically navigated to the deployment point in the heart with the aid of a magnetic balloon adjacent the distal end 26 of the delivery catheter. As shown in FIG. 4, the catheter 20" is similar to catheter 20, and corresponding parts are identified with corresponding reference numerals. However, catheter 20" has an inflatable chamber 54 formed in the sidewall 56 adjacent the distal end 26. A passage 58 extends through the sidewall from the proximal end to the inflatable chamber. The delivery catheter 20" is introduced into the patient's vasculature. The inflatable chamber 54 is inflated by injecting a magnetic fluid through passage 58 and into the chamber. The elongate inflated chamber 54 makes the distal end of the delivery catheter 20" magnetically responsive, and the delivery catheter can be advanced through the vasculature by applying an external magnetic field in the appropriate direction to orient the elongate inflated chamber, and thus the distal end 24 of the delivery catheter 20", in the desired direction of movement. The delivery catheter 20" can then be advanced by pushing the proximal end. If the applied field includes a magnetic gradient, the field can also be used to advance the balloon 54, and thus the distal end of the catheter, in the desired direction. Once the distal end 24 of the delivery catheter 20" reaches the deployment point, the inflatable chamber 54 can be deflated by withdrawing the magnetic fluid through the passage 58. Thus, the distal end of the catheter 20" can selectively be made magnetically responsive. Of course some other method of selectively making the distal end of the delivery catheter magnetically responsive could also be used. For example, one or more electromagnetic coils could be incorporated into the distal end, and electric current selectively applied to the one or more coils to temporarily make the distal end magnetically responsive.

The inflatable chamber 54 also functions to block the coronary venous vasculature, to facilitate the injection of contrast media into the venous system for imaging, to facilitate the placement of the pacing leads. For this reason, the inflatable chamber 54 could be provided on the catheter 20 or 20'.

Figure 5:
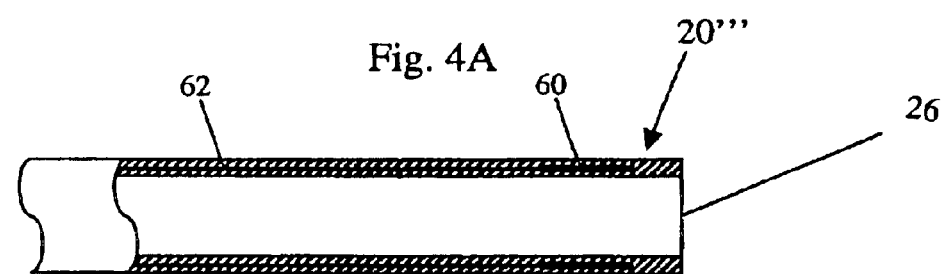
FIG. 5 is a partial cross-sectional view of the distal end of a delivery catheter used to deploy pacing leads in accordance with this invention, with an electromagnetic coil therein for facilitating magnetic navigation of the delivery catheter.

According to a fifth embodiment of this invention shown in FIG. 5, the distal end 24 of the delivery catheter 20''' is magnetically navigated to the deployment point in the heart selectively applying current to a coil in th distal end of the catheter 20''' to make distal end of the catheter magnetically responsive. The catheter 20''' is similar to catheter 20, except that catheter 20" includes a coil 60 in the sidewall of the cannula, adjacent the distal end, connected to leads 62 and 64 that extends to the proximal end of the catheter. The distal end of the delivery catheter 20''' can be selectively made magnetically responsive by connecting the leads 62 and 64 to a source of electric power. Then, by applying an external magnetic field, he distal end of the catheter can be navigated. The distal end of the delivery catheter 2''' aligns with the applied magnetic field, and can be advanced in the selected direction by pushing the proximal end of the delivery catheter. If the magnetic field include a magnetic gradient, the field can also be used to advance the distal end of the catheter in the desired direction.

Figure 6:
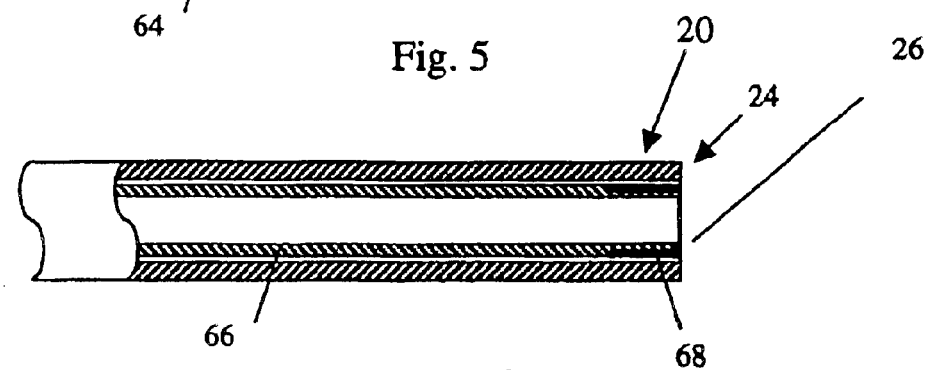
FIG. 6 is a partial cross-sectional view of the distal end of a telescoping delivery catheter used to deploy pacing leads in accordance with this invention, shown with the telescoping member in its retracted position.
Figure 6A:
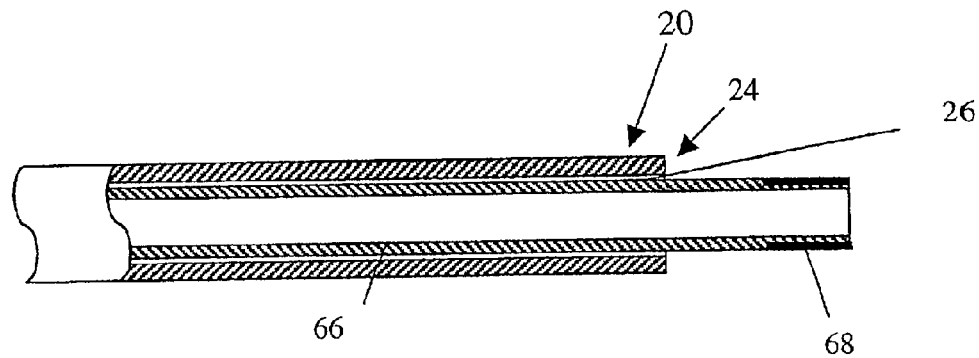
FIG. 6A is a partial cross-sectional view of the distal end of a telescoping delivery catheter used to deploy pacing leads in accordance with this invention, shown with the telescoping member partially extended.

According to a fifth embodiment of this invention, shown in FIGS. 6 and 6A, the delivery catheter 20 includes a telescoping member. First the delivery catheter is magnetically navigated to a desired location, and then the telescoping member is deployed from the distal end of the delivery catheter and magnetically navigated deeper into the coronary venous vasculature. A telescoping member 66 is disposed inside the lumen 26 of the delivery catheter 20, and has a magnetic body 68 adjacent the distal end. When the telescoping member is in its retracted position (shown in FIG. 6) the magnetic body 68 on the telescoping member 66 allows the distal end 24 of the delivery catheter 20 to be magnetically navigated. The catheter 20 is introduced into the patient's vasculature, and advanced through the vasculature by applying an external magnetic field in the appropriate direction to orient the magnetic body 68, and thus the distal end 24 of the delivery catheter 20, in the desired direction of movement. If the applied field includes a magnetic gradient, the field can also be used to advance the magnetic body, in the desired direction. The delivery catheter 20 can then be advanced by pushing the proximal end of the delivery catheter 20. Once the distal end of the delivery catheter is at its desired location, the telescoping member 66 is deployed from the distal end 24 of the catheter 20. The telescoping member 66 is advanced through the vasculature by applying an external magnetic field in the appropriate direction to orient the magnetic body 68, and thus the distal end of the telescoping member 66, in the desired direction of movement. The telescoping member can then be advanced by pushing its proximal end. If the applied field includes a magnetic gradient, the field can also be used to advance the magnetic body, in the desired direction. Of course a tethered magnet or a magnetic stylette, or some other means described herein can be used to magnetically navigate the telescoping member 66.

Once the distal end of the delivery catheter 20 or 20' is a the selected deployment point the pacing leads are deployed from the distal end of the catheter. The pacing leads are preferably magnetically deployed. While in he preferred embodiment of this invention both the delivery catheter and the pacing leads are magnetically navigated, either the delivery catheter or the pacing leads could be navigated conventionally, if desired, without departing from the principles of this invention.

Figure 7:
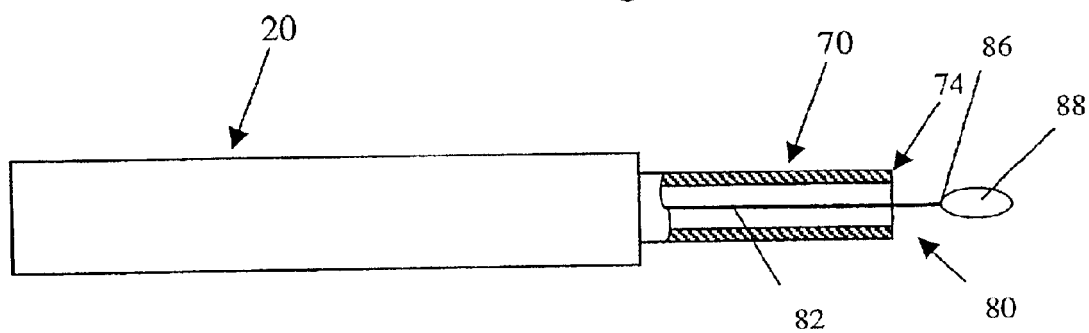
FIG. 7 is a partial cross-sectional view of a pacing lead in accordance with this invention, shown as it would be deployed from a delivery catheter and navigated with a guide wire.

A first method of magnetically navigating the pacing leads is shown in FIG. 7, where the distal end of a pacing lead 70 is magnetically navigated to the pacing site in the heart by using a magnetic guide wire. The pacing lead 70 has a proximal end, an open distal end 74, and a lumen 76 therebetween. There are electrodes adjacent the distal end 74 of the pacing lead 70, connected to leads extending along the pacing lead for supplying electric power to the electrodes. The guide wire 80 comprises a flexible wire 82, having a proximal end and a distal end 86, with a magnetic body 88 on its distal end. The flexibility of the flexible wire 82 may vary along its length, preferably increasing in flexibility toward the distal end 86. The magnetic body 88 may be either a permanent magnetic material or a permeable magnetic material. The pacing lead 70 is inserted through the lumen 76 of the delivery catheter (e.g., catheter 20, 20' 20" or 20''') the guide wire 80 is advanced through the open distal end of the pacing lead. The guide wire 80 and the pacing lead 70 are advanced through the vasculature by applying an external magnetic field in the appropriate direction to orient the magnetic body 88, and thus the distal end 86 of the guide wire 80, in the desired direction of movement. The guide wire 80 can then be advanced by pushing the proximal end. The pacing lead 70 is then advanced over the guide wire 80. If the applied magnetic field includes a magnetic gradient, the magnetic field may also act to advance the magnet body 88, and thus the guide wire 80. The guide wire 80 is successively advanced ahead of the pacing lead 70, and the pacing lead is successively advanced over the guide wire, until the distal end of the pacing lead reaches the pacing point.

Figure 8:
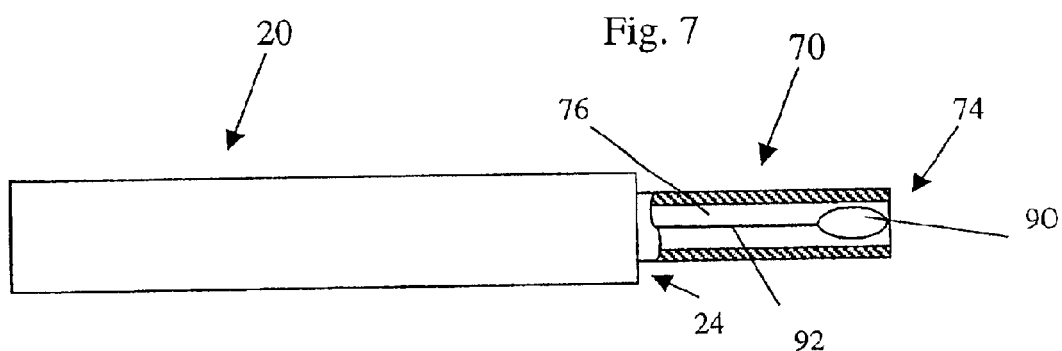
FIG. 8 is a partial cross-sectional view of a pacing lead in accordance with this invention, shown as it would be deployed from a delivery catheter and navigated with a tethered magnetic body.

A second method of magnetically navigating the pacing leads is shown in FIG. 8, where the distal end of a pacing lead 70 is magnetically navigated to the pacing site in the heart by using a magnetic guide wire. The distal end 74 of the pacing lead 70 is magnetically navigated to the pacing point in the heart by using a magnetic body 90, disposed in the lumen 76 of the pacing lead, adjacent the distal end. The magnetic body 90 may be either a permanent magnetic material or a permeable magnetic material. The magnetic seed 90 is attached to a tether 92 extending through the lumen 76 of the pacing lead to the proximal end. The tether 92 helps retain the magnetic seed 90 in the lumen 76 of the pacing lead 70, and allows the magnetic seed 80 to be withdrawn from the pacing lead once the distal end 74 of the pacing catheter has been navigated to the pacing point. The pacing lead 70 and magnetic body 90 are deployed from the distal end of the delivery catheter, and advanced through the vasculature by applying an external magnetic field in the appropriate direction to orient the magnetic seed 90, and thus the distal end 74 of the pacing lead 70, in the desired direction of movement. The pacing lead 70 can then be advanced by pushing the proximal end. If the externally applied magnetic field include a magnetic gradient, the magnetic field may also apply a force advancing the magnetic body 90 and thus the distal end 74 of the pacing lead 70. Once the distal end 74 of the pacing lead 70 reaches the pacing point, the magnet seed 90 is removed through the lumen 96 by pulling the tether 92.

Figure 8A:
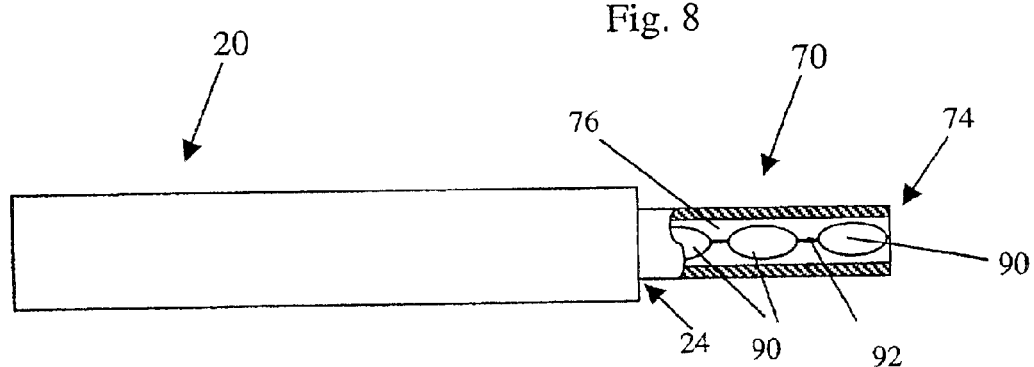
FIG. 8A is a partial cross-sectional view of a pacing lead in accordance with this invention, shown as it would be deployed from a delivery catheter and navigated with a plurality of tethered magnetic bodies.

An alternate construction of the second embodiment is shown in FIG. 8A, where instead of one magnetic body 90 on the distal end of the tether 92, there are a plurality of magnetic bodies 90 on the distal end portion of the tether. The plurality of magnetic bodies 90 facilitates the navigation of the distal end of the pacing lead 70, causing the entire distal end portion to align with the field. While the magnetization direction of the magnetic bodies would conventionally be axial, parallel to the tether, in some applications it might be desirable to have the magnetization direction of each magnetic body 90 be vary from axial so that when a magnetic field is applied to the magnet bodies 90 on the tether 92, the pacing lead 70 assumes a predetermined shape as the magnet bodies align with the applied magnetic field. This is illustrated in FIGS. 13A and 13B, and described above.

Figure 9:
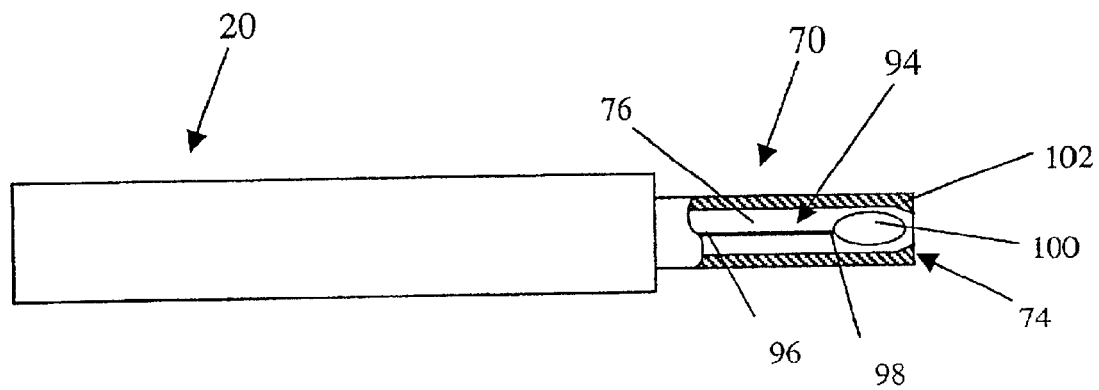
FIG. 9 is a partial cross-sectional view of a pacing lead in accordance with this invention, shown as it would be deployed from a delivery catheter and navigated with a magnetic stylette.

A third method of magnetically navigating the pacing leads is shown in FIG. 9, where the distal end 74 of the pacing lead 70 is magnetically navigated to the pacing point in the heart by using a magnetic stylette 94, disposed in the lumen 76 of the pacing lead 70. The stylette 94 comprises a flexible shaft 96 having a proximal end, a distal end 98, and a magnetic body 100 on the distal end. The shaft 96 is sufficiently flexible to allow the stylette to flex under the applied magnetic field and conform to the tortuous path through the vasculature, but is sufficiently stiff to apply a pushing force to the pacing lead 70.

The stylette 94 can be inserted into the lumen 76 of the pacing lead 70, with the distal end of the stylette engaged by a stricture formed by an annular collar 102 on the inside of the lumen 76, so that the magnetic seed 100 of the stylette 94 is retained in the lumen. Once the pacing lead 70 is at the pacing site, the stylette 94 can be removed from the lumen 76. The pacing lead 70 with the stylette 94 in the lumen 76 are deployed from the distal end of the delivery catheter, and advanced through the vasculature by applying an external magnetic field in the appropriate direction to orient the magnetic seed 90, and thus the distal end 74 of the pacing lead 70, in the desired direction of movement. The pacing lead 70 can then be advanced by pushing the proximal end of either the pacing lead 70, or preferably of the stylette 94. If the externally applied magnetic field includes a magnetic gradient, the field may also apply a sufficient pulling force to move the magnetic body 100 and thus the distal end 74 of the pacing lead. Once the distal end 74 of the pacing lead 70 reaches the pacing site, the stylette 94 is withdrawn from the delivery catheter through the proximal end.

Figure 9A:
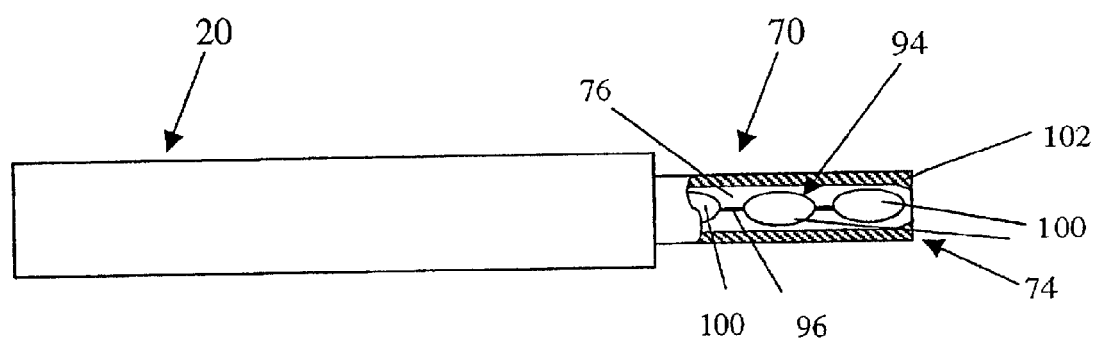
FIG. 9A is a partial cross-sectional view of a pacing lead in accordance with this invention, shown as it would be deployed from a delivery catheter and navigated with a magnetic stylette having a plurality of magnetic bodies.

An alternate construction of the third method is shown in FIG. 9A, where instead of one magnetic body 100 on the distal end of the tether 94, there are a plurality of magnetic bodies 100 on the distal end portion of the tether. The plurality of magnetic bodies 100 facilitate the navigation of the distal end of the pacing lead, causing the entire distal end portion to align with the field. While the magnetization direction of the magnetic bodies would conventionally be axial, parallel to the shaft of the stylette 94, in some applications it might be desirable to have the magnetization direction of each magnetic body 100 vary from axial so that when a magnetic field is applied to the magnet bodies 100 on the tether 94, the pacing lead assumes a predetermined shape as the magnet bodies align with the applied magnetic field. This is illustrated in FIGS. 13A and 13B, and described above.

Figure 10:
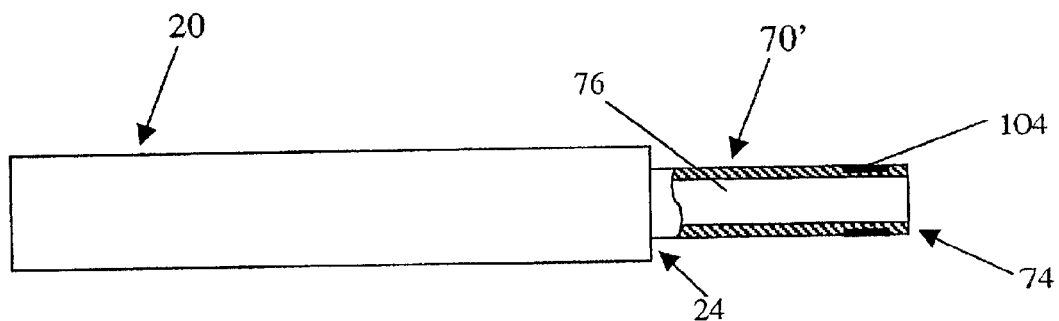
FIG. 10 is a partial cross-sectional view of a pacing lead in accordance with this invention, show as it would be deployed from a delivery catheter, having a magnetic body for facilitating magnetic navigation of the magnetic stylette.

A fourth method of magnetically navigating the pacing leads is shown in FIG. 10, in which the pacing lead 70' is specially constructed to include a magnetic body. The pacing lead 70' is similar to pacing lead 70, and corresponding parts are identified with corresponding reference numerals. However, pacing lead 70' includes a magnetic body 104, which makes the pacing lead 70' magnetically responsive.

The pacing lead 70' is introduced from the distal end of the delivery catheter, and advanced through the vasculature by applying an external magnetic field in the appropriate direction to orient the magnetic body 104, and thus the distal end of the pacing lead, in the desired direction of movement. The pacing lead can then be advanced by pushing the proximal end. After distal end 74 of the pacing lead 70' has been placed at the pacing site, the magnetic body 104 preferably gradually loses its magnetic responsiveness, e.g. through oxidation of a ferromagnetic material. Of course some other method of temporarily making the distal end of the pacing lead 70' could also be used. For example, one or more electromagnetic coils could be incorporated into the distal end, and electric current selectively applied to the one or more coils to temporarily make the distal end magnetically responsive.

Figure 11:
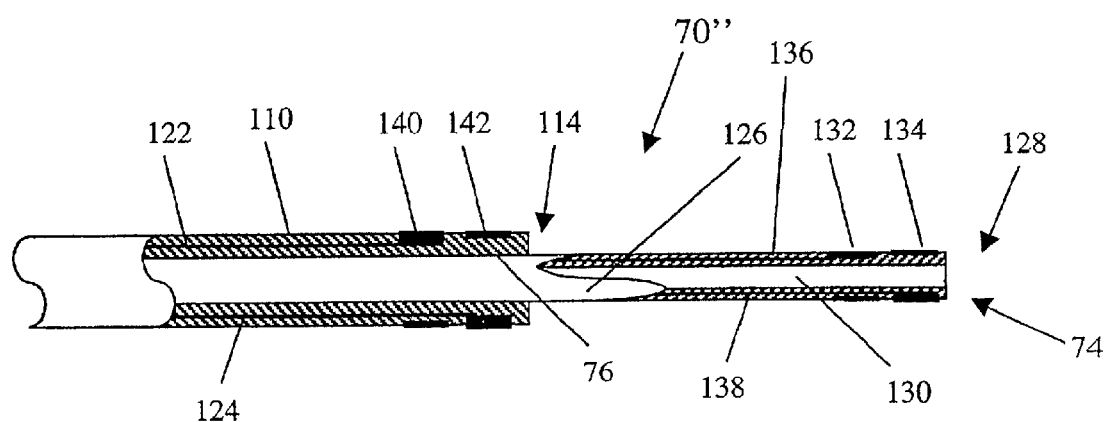
FIG. 11 is a partial cross-sectional view of the distal end of a telescoping, multiple pacing lead constructed according to the principles of this invention.

A telescoping, multiple electrode pacing lead constructed according to the principles of this invention is indicated generally as 70' in FIG. 11. The pacing lead 70 has a side wall 110, with a proximal end and a distal end 114, an a lumen therebetween. There are electrodes 118 and 120 on the sidewall 110, adjacent the distal end 114. Leads 122 and 124 extend to the electrodes 118 and 120, respectively, to provide a pacing current to the electrodes. A telescoping section 126 telescopes in the lumen of the pacing lead 70". The telescoping section 126 has proximal end, a distal end 128, and a lumen 130 therebetween. There are electrodes 132 and 134 on the sidewall 136, adjacent the distal end 128. Leads 136 and 138 extend to the electrodes 132 and 134, respectively to provide a pacing current to the electrodes. The telescoping multiple electrode pacing lead allows pacing at two separate sites spaced at a distance that can be determined by the physician at the time of placement. The pacing lead 70" is delivered to a point adjacent the heart in a cannula, an introduced through the wall of the pericardial sack, and navigated through the pericardial pace, until the pairs of electrodes are appropriately positioned on the epicardium. The telescoping section 126 allows the physician to select the spacing between the electrode pairs.

Either the delivery catheters 20 and/or the pacing leads 70 can be constructed with a highly flexible portion proximal to the distal-most magnetic body. This highly flexible portion acts like a hinge, allowing the catheter or the pacing lead into which it is incorporated to make sharp turns when the appropriate magnetic field is applied.

Figure 12:
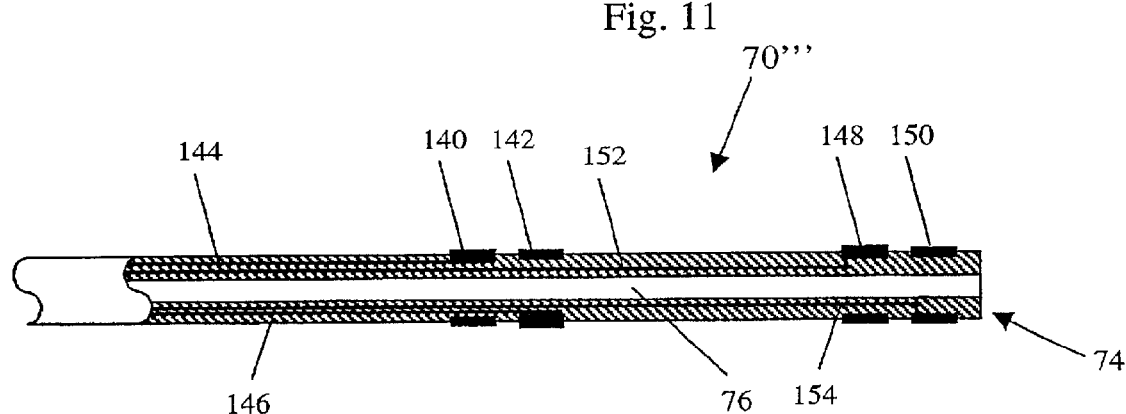
FIG. 12 is a partial cross-sectional view of a multiple pacing lead of the present invention.

A multiple electrode pacing lead constructed according to the principles of this invention is indicated generally as 70''' in FIG. 12. The pacing lead 70''' has a proximal end, a distal end 74, and a lumen 76 therebetween. There are electrodes 140 and 142 on the sidewall, spaced from the distal end 74. Leads 144 and 146 extend to the electrodes 118 and 120, respectively, to provide a pacing current to the electrodes. There are electrodes 148 and 150 on the sidewall, adjacent the distal end 74. Leads 152 and 154 extend to the electrodes 148 and 150, respectively. The pacing lead 70''' is delivered to a point adjacent the heart in a cannula, an introduced through the wall of the pericardial sack, and navigated through the pericardial space, until the pairs of electrodes are appropriately positioned on the epicardium. This allows bi-ventricular pacing with the placement of a single pacing lead.

Figure 14A:
FIG. 14A is a cross-sectional view of a pacing lead showing external eyelets for receiving a guiding member, such as a guide wire or stylette.
Figure 14B:
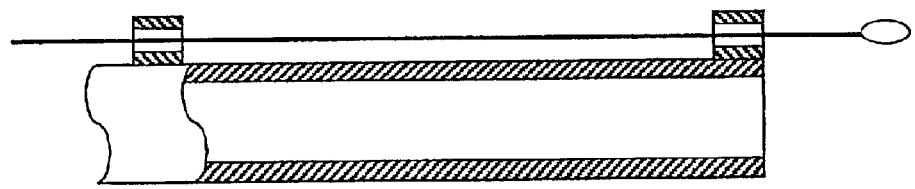
FIG. 14B is a cross-sectional view of a delivery catheter showing external eyelets for receiving a guiding member, such as a guide wire or stylette.

FIGS. 14A and 14B show an alternate embodiment of both a pacing lead and a delivery catheter, having external eyelets through which a guide wire with a magnet, a stylette, or other device can extend to guide the pacing lead or delivery catheter.

Figure 15A:
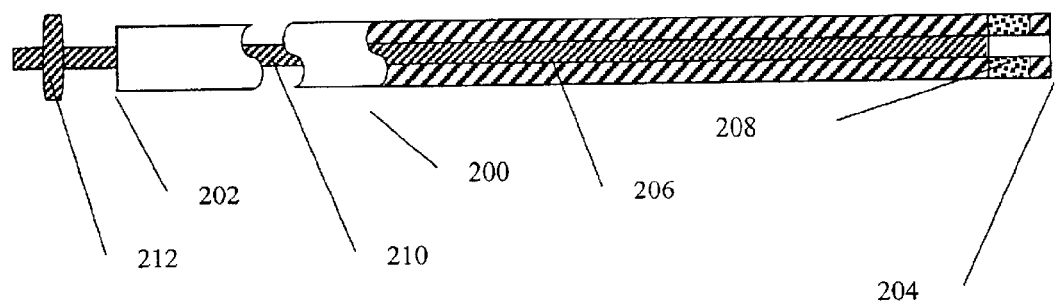
FIG. 15A is a longitudinal cross-sectional view of a magnetic stylette for navigating a delivery catheter.

A first embodiment of a magnetic stylette for use in magnetically navigating a delivery catheter is indicated generally as 200 in FIG. 15A. The stylette has a proximal end 202, a distal end 204, and a lumen 206 therebetween. The stylette 200 may be made of a flexible polymeric tube. The stylette 200 preferably increases in flexibility in the distal direction, and particularly at the distal end adjacent the distal end so that the distal end of the stylette orients in response to a magnetic field, as described below. The stylette is preferably sufficiently stiff, however, to be able to push a delivery catheter into which it is inserted. There is a magnetically responsive body 208 adjacent the distal end of the stylette 200. The magnetically responsive body may either be a permanent magnetic material or a permeable magnetic material. A stiffening wire 210 is adapted to be inserted into the lumen 206 of the stylette 200, to selectively stiffen the stylette. The wire can be made of a metal or polymeric material, and can taper or otherwise increase in flexibility toward the distal end. The wire 210 can be inserted into the lumen 206 to increase the stiffness of the stylette 200, or removed to increase the flexibility of the stylette. The stiffening wire 210 preferably includes a stop 212 that engages the proximal end of the stylette to prevent the wire from protruding from the distal end of the stylette.

Figure 15B:
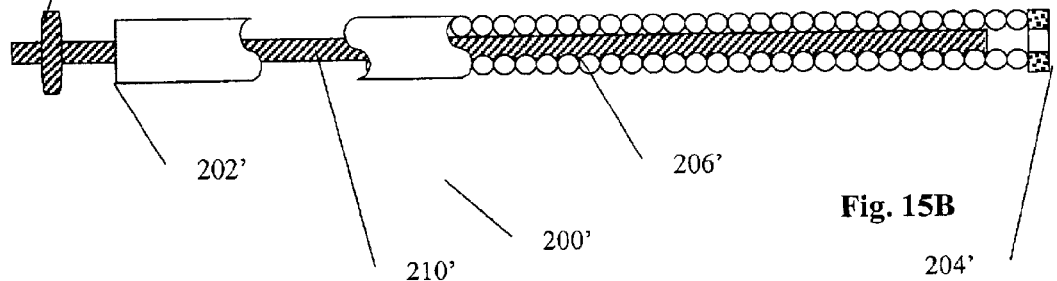
FIG. 15B is a longitudinal cross-sectional view of an alternate construction of a magnetic stylette for navigating a delivery catheter.

A second embodiment of a magnetic stylette for use in magnetically navigating a delivery catheter is indicated generally as 200' in FIG. 15B. The stylette has a proximal end 202' a distal end 204', and a lumen 206' therebetween. The stylette 200' may be made of a metal or plastic coil, which may be enclosed is a thin walled, resilient jacket. The stylette 200' preferably increases in flexibility in the distal direction, and particularly at the distal end adjacent the magnetically responsive body 208 so that the distal end of the stylette orients in response to a magnetic field, as described below. The stylette is preferably sufficiently stiff, however, to be able to push a delivery catheter into which it is inserted. There is a magnetically responsive body 208' adjacent the distal end of the stylette 200'. The magnetically responsive body may either be a permanent magnetic material or a permeable magnetic material. A stiffening wire 210' is adapted to be inserted into the lumen 206' of the stylette 200', to selectively stiffen the stylette. The wire can be made of a metal or polymeric material, and can taper or otherwise increase in flexibility toward the distal end. The wire 210' can be inserted into the lumen 206' to increase the stiffness of the stylette 200', or removed to increase the flexibility of the stylette. The stiffening wire 210' preferably includes a stop 212' that engages the proximal end of the stylette to prevent the wire from protruding from the distal end of the stylette.

The methods and apparatus of the present invention are particular adapted for remote control implementation. An automatic advancer can be provided to automatically advance the delivery catheter and the pacing leads. A user interface, using bi-planar fluoroscopic imaging, allows the physician to quickly indicate the desired direction on two two-dimensional images, which a computer can translate the selection to a direction in three dimensional space and control an external magnet (which may be a permanent magnet or magnets, an electromagnet or electromagnets, or a superconducting electromagnet or superconducting electromagnet) to apply the appropriate magnetic field. Once the magnet properly orients the device, the device can be advanced using an automatic advancer, or if the magnet is capable of generating a sufficient gradient, using the external magnets. This automation means that the physician can be located away from the x-ray of the bi-planer x-ray imaging apparatus, and can even be located away from the patient. Thus with the methods and apparatus of the present invention, pacing leads and be quickly and accurately delivered to the pacing points, shortening procedures and the resulting stress on the patient.

What is claimed is:

1. A method of placing a pacing lead in the heart, the method comprising: introducing a distal end of a delivery catheter into the patient's vasculature; magnetically navigating the distal end of the delivery catheter to the patient's heart by extending a guide wire having a magnetically responsive seed thereon through the lumen of the delivery catheter; applying a magnetic field to orient he seed on the guide wire in the desired direction, advancing the guide wire in the desired direction relative to the delivery catheter, and advancing the delivery catheter over the guide wire; deploying a pacing lead from the distal end of the delivery catheter; and magnetically navigating the pacing lead to the pacing application site.

2. A method of placing a pacing lead in the heart, the method comprising: introducing a distal end of a delivery catheter into the patient's vasculature; magnetically navigating the distal end of the delivery catheter to the patient's heart by providing a magnetically responsive seed in the lumen of the delivery catheter adjacent the distal end, the magnetic seed having a tether thereon, applying a magnetic field to orient the seed, and thus the distal end portion of the delivery catheter in the desired direction, advancing the catheter in the desired direction, and further comprising the step of removing the magnetically responsive seed from the lumen of the catheter with the tether when the distal end of the delivery catheter is in the desired location in the heart; deploying a pacing lead from the distal end of the delivery catheter; and magnetically navigating the pacing lead to the pacing application site.

3. A method of placing a pacing lead in the heart, the method comprising: introducing a distal end of a delivery catheter into the patient's vasculature; magnetically navigating the distal end of the delivery catheter to the patient's heart by inserting a stylette having a magnetically responsive seed thereon into the lumen of the delivery catheter so that the seed is adjacent the distal end, applying a magnetic field to orient the seed, and thus the distal end portion of the delivery catheter in the desired direction, advancing the catheter in the desired direction by pushing the catheter and/or the stylette, and further comprising the step of removing the stylette from the lumen of the catheter when the distal end of the delivery catheter is in the desired location in the heart; deploying a pacing lead from the distal end of the livery catheter; and magnetically navigating the pacing lead to the pacing application site.

4. A method of placing a pacing lead in the heart, the method comprising: introducing a the distal end of a delivery catheter into the patient's vasculature, the delivery catheter comprising an inflatable balloon adjacent the distal end; magnetically navigating the distal end of the delivery catheter to the patient's heart by inflating the balloon with a magnetically responsive material, applying a magnetic field to orient the balloon on the distal end portion of the delivery catheter in the desired direction, advancing the catheter in the desired direction; and further comprising the step of removing the magnetically responsive material from the balloon when the distal end of the delivery catheter is in the desired location in the heart; deploying a pacing lead from the distal end of the delivery catheter; and magnetically navigating the pacing lead to the pacing application site.

5. A method of placing a pacing lead in the heart, the method comprising: introducing a distal end of a delivery catheter into the patient's vasculature; magnetically navigating the distal end of the delivery catheter to the patient's heart; deploying a pacing lead from the distal end of the delivery catheter; and magnetically navigating the pacing lead to the pacing application site by extending a guide wire having a magnetically responsive seed thereon through the lumen of the pacing lead; applying a magnetic field to orient the seed on the guide wire in the desired direction, advancing the guide wire in the desired direction relative to the pacing lead, and advancing the pacing lead over the guide wire.

6. A method of placing a pacing lead the heart, the method comprising: introducing a distal end of a delivery catheter into the patient's vasculature; magnetically navigating the distal end of the delivery catheter to the patient's heart; deploying a pacing lead from the distal end of the delivery catheter; and magnetically navigating the pacing lead to the pacing application site by providing a magnetically responsive seed in the lumen of the pacing lead adjacent the distal end, the magnetic seed having a tether thereon, applying a magnetic field to orient the seed, and thus the distal end portion of the pacing lead in the desired direction, advancing the pacing lead in the desired direction, and further comprising the step of removing the magnetically responsive seed from the lumen of the pacing lead with the tether when the distal end of the pacing lead is in the desired location at the pacing site.

7. A method of placing a pacing lead in the heart, the method comprising: introducing a distal end of a delivery catheter into the patient's vasculature; magnetically navigating the distal end of the delivery catheter to the patient's heart; deploying a pacing lead from the distal end of the delivery catheter; and magnetically navigating the pacing lead to the pacing application site by inserting a stylette having a magnetically responsive seed thereon into the lumen of the pacing lead so that the seed is adjacent the distal end, applying a magnetic field to orient the seed, and thus the distal end portion of the pacing lead in the desired direction, advancing the catheter in the desired direction by pushing the catheter and/or the stylette, and further comprising the step of removing the stylette from the lumen of the pacing lead when the distal end of the pacing lead catheter is in the desired location at the pacing site.

8. A method of placing a pacing lead including a magnetically responsive body in the heart, method comprising: introducing a the distal end of a delivery catheter into the patient's vasculature; magnetically navigating, the distal end of the delivery catheter to the patient's heart; deploying a pacing lead from the distal end of the delivery catheter; and magnetically navigating the pacing lead to the pacing application site by applying a magnetic field to orient a balloon on the distal end portion of the delivery catheter in the desired direction, advancing the pacing lead in the desired direction.

9. The method according to claim 8 wherein the magnetically responsive body on the pacing lead loses responsiveness with time.

* * * * *